United States Patent [19]

Taylor

[11] Patent Number: 4,619,262
[45] Date of Patent: Oct. 28, 1986

[54] SURGICAL STAPLING DEVICE

[75] Inventor: James Taylor, Droitwich, England

[73] Assignee: Syncare, Inc., Branchburg, N.J.

[21] Appl. No.: 741,483

[22] Filed: Jun. 5, 1985

[30] Foreign Application Priority Data

Jul. 10, 1984 [GB] United Kingdom ............... 8417562

[51] Int. Cl.⁴ .......................... A61B 17/04; B31B 1/00
[52] U.S. Cl. ........................ 128/334 R; 227/DIG. 1; 227/19
[58] Field of Search ................... 128/334 R; 227/19

[56] References Cited

U.S. PATENT DOCUMENTS 4,411,378 10/1983 Warman ...................... 128/334 R

FOREIGN PATENT DOCUMENTS 0069557 12/1983 European Pat. Off. ............ 227/901
8102269 8/1981 PCT Int'l Appl. .................... 227/19
8202486 8/1982 PCT Int'l Appl. .................... 227/19

*Primary Examiner*—Richard C. Pinkham
*Assistant Examiner*—Gary Jackson
*Attorney, Agent, or Firm*—Michael Ebert

[57] ABSTRACT

A surgical stapling device loaded with staples each having a pair of parallel limbs bridged by a straight crosspiece. In operation, as the limbs are implanted by the device on opposite sides of a skin incision, they are bent inwardly toward each other below the skin surface to close the incision, the crosspiece being bent to create an arched air gap above the skin surface to allow space for post-operative swelling and to facilitate subsequent removal of the staple. In the device, a row of staples straddling a rail are advanced toward a metal mandrel projecting from the front end of the rail into an outlet. The mandrel, which has an arched formation, is flanked by a pair of abutments on the front end of the rail whereby the foremost staple in the advancing row is deposited onto the mandrel. Cooperating with the mandrel is a plate-like former whose leading edge has a recess therein leading to an inner arched section which conforms to the arched mandrel. When the device is actuated, the leading edge of the former which is normally retracted from the mandrel, advances toward the mandrel, the former sliding along the end abutments of the rail and causing the staple engaged thereby to emerge from the outlet, in the course of which movement the staple is implanted in the skin and is formed on the mandrel to assume the desired configuration.

9 Claims, 12 Drawing Figures

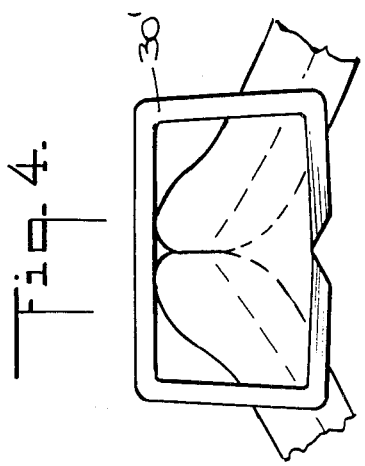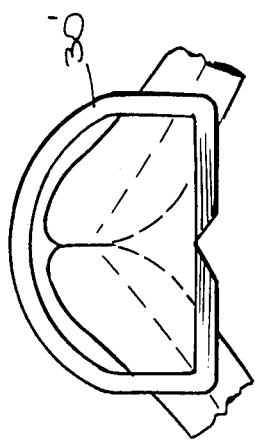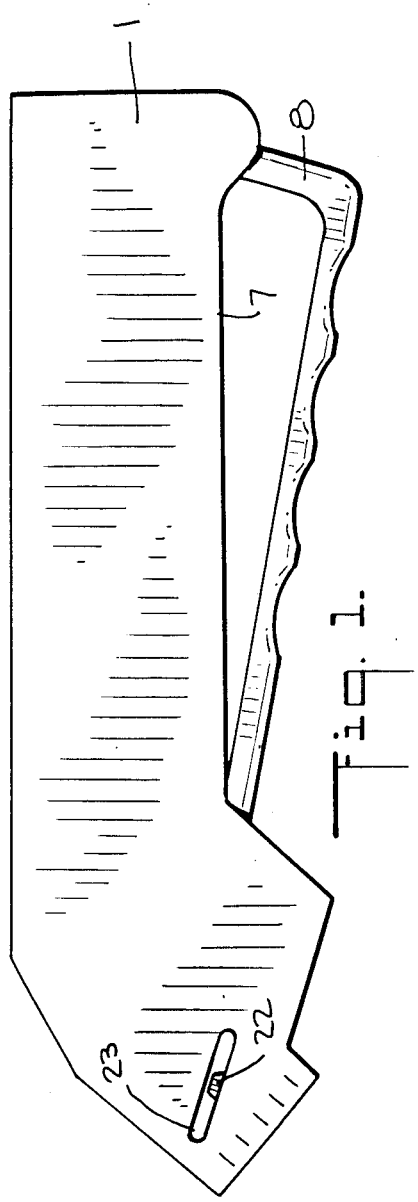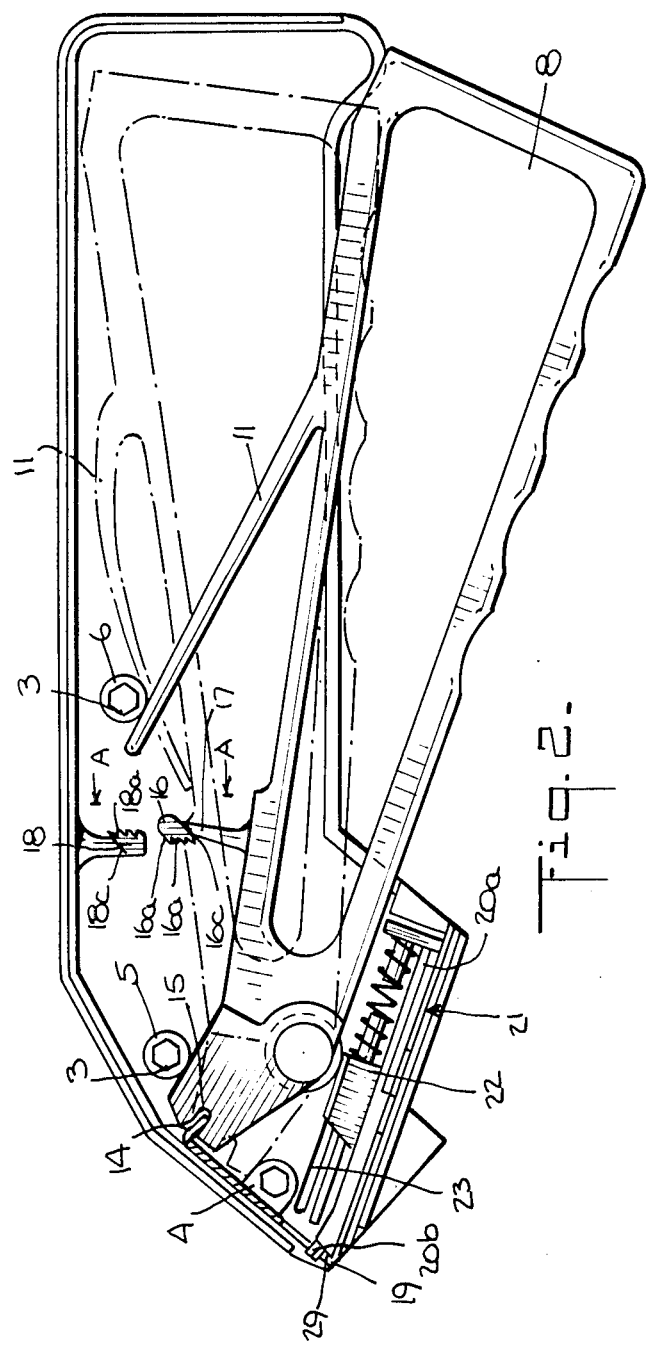

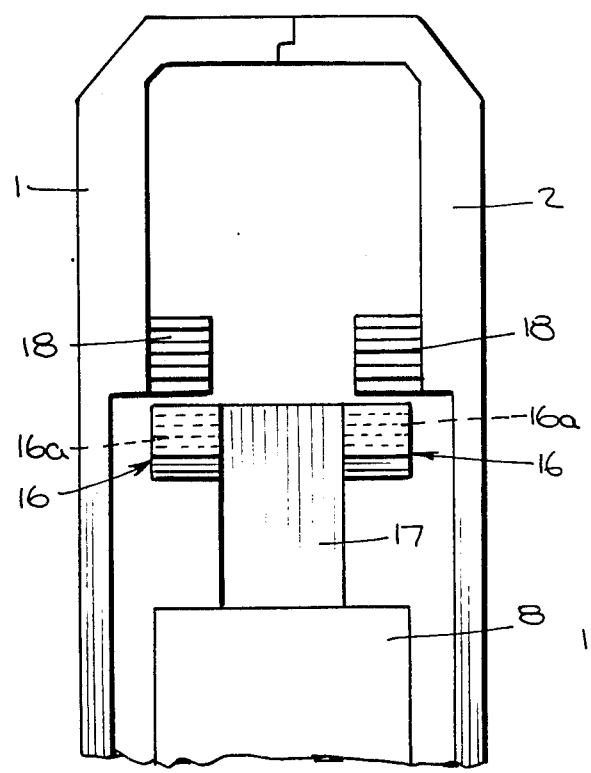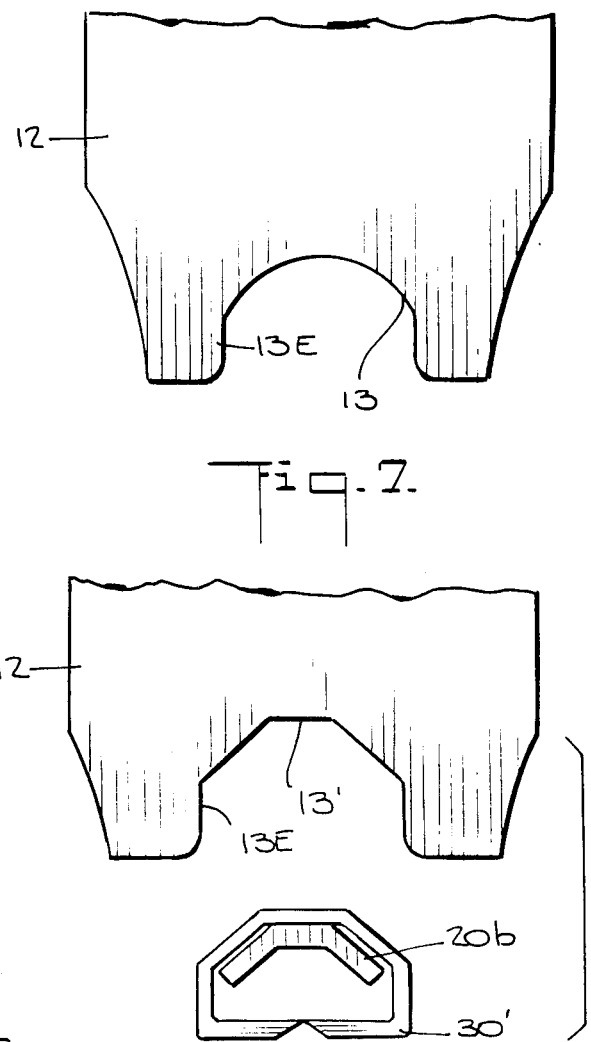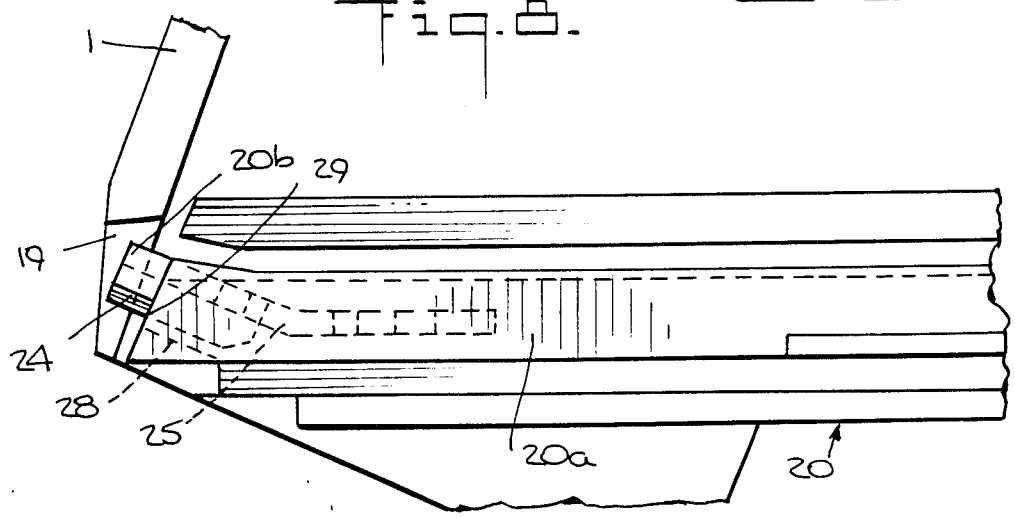

SURGICAL STAPLING DEVICE

BACKGROUND OF INVENTION

1. Field of Invention

This invention relates generally to surgical stapling devices, and more particularly to a device which forms a standard surgical staple having a pair of parallel limbs bridged by a straight crosspiece whereby when the device is actuated, the limbs are implanted on opposite sides of a skin incision and are bent inwardly toward each other below the skin surface to close the incision, the crosspiece being bent to create an arched air gap above the skin surface to allow space for post-operative swelling and to facilitate subsequent removal of the staple.

2. Status of Prior Art

In surgical procedures, the conventional skin closure technique involves a needle and a suture thread. Such suturing leaves crosshatching across the scar line as a result of pressure applied to the region during the healing process. It has therefore become cosmetically desirable to achieve an effective wound closure with the minimum amount of crosshatching.

The use of surgical stapling devices is well known. These devices make use of standard staples having a pair of parallel limbs bridged by a straight crosspiece, the limbs being implanted in the skin on opposite sides of the incision and being bent inwardly toward each other to form a loop closing the incision.

Surgeons have been making increasing use of surgical stapling devices rather than conventional thread sutures in that it is a less difficult and much faster procedure. The use of surgical staples reduces the time required for suturing and hence the length of time a patient must be maintained under anaesthesia.

Among prior art patents which disclose surgical staplers are the Becht U.S. Pat. Nos. 4,179,057 and 4,109,844, and the Warman, U.S. Pat. No. 4,411,378. Also of prior art interest are Fishberg, U.S. Pat. No. 3,873,016; Hasaka, U.S. Pat. No. 3,889,338; and Furutu, U.S. Pat. No. 4,187,970.

In the course of healing, all wounds swell due to edema, thereby filling the air gap between the wound and the straight crosspiece of the staple and giving rise to crosshatching. Thus known types of surgical staplers do not overcome the cross-hatching problem and its adverse effects. Moreover, because the air gap is filled with swollen tissue, it becomes difficult when the staples are later to be removed from the wound, to insert the staple remover under the staple crosspiece without inflicting tissue trauma and thereby causing discomfort to the patient.

SUMMARY OF INVENTION

In view of the foregoing, the main object of this invention is to provide an improved surgical stapling device for closing incisions made in the skin.

More particularly, an object of this invention is to provide a surgical stapling device which implants standard surgical staples into the skin and so forms the staple as to raise a portion thereof above the skin surface to create an arched air gap having the following advantages:

A. The raised staple allows space for edema or post-operative swelling.

B. It lessens scarring and crosshatching, for it does not strangulate the skin tissue.

C. It facilitates subsequent removal of the staple in that it permits easy insertion of the staple remover under the staple crosspiece, thereby minimizing tissue trauma and discomfort to the patient.

Also an object of the invention is to provide a surgical stapling device which prevents undesirable twisting of the staple during its formation.

Yet another object of the invention is to provide a device of simple, yet efficient and reliable construction, whereby the surgical stapling device may be made in low-cost disposable form.

Briefly stated, these objects are attained in a surgical stapling device loaded with staples each having a pair of parallel limbs bridged by a straight crosspiece. In operation, as the limbs are implanted by the device on opposite sides of a skin incision, they are bent inwardly toward each other below the skin surface to close the incision, the crosspiece being bent to create an arched air gap above the skin surface to allow space for post-operative swelling and to facilitate subsequent removal of the staple. In the device, a row of staples straddling a rail are advanced toward a metal mandrel projecting from the front end of the rail into an outlet. The mandrel, which has an arched formation, is flanked by a pair of abutments on the front end of the rail whereby the foremost staple in the advancing row is deposited onto the mandrel. Cooperating with the mandrel is a plate-like former whose leading edge has a recess therein leading to an inner arched section which conforms to the arched mandrel. When the device is actuated, the leading edge of the former which is normally retracted from the mandrel, advances toward the mandrel, the former sliding along the end abutments of the rail and causing the staple engaged thereby to emerge from the outlet, in the course of which movement the staple is implanted in the skin and is formed on the mandrel to assume the desired configuration.

OUTLINE OF DRAWINGS

For a better understanding of the invention as well as other objects and further features thereof, reference is made to the following detailed description to be read in conjunction with the accompanying drawings, wherein:

FIG. 1 is a side view of a surgical stapling device according to the invention;

FIG. 2 is a schematic illustration of the device shown with a housing part removed;

FIG. 3 is a sectional view in a larger scale along the plane indicated by line A—A in FIG. 2;

FIG. 4 is a diagrammatic view of a skin incision closed by a conventional staple;

FIG. 5 is a diagrammatic view of a skin incision closed by a staple formed by a device according to the invention;

FIG. 6 is an end view of the former included in the device of FIGS. 1 to 3;

FIG. 7 is an end view of an alternative embodiment of former and a mandrel usable in a device according to the invention;

FIG. 8 is a side view of the mandrel and rail included in the embodiment of the invention shown in FIG. 2;

DESCRIPTION OF INVENTION

Figure 9:
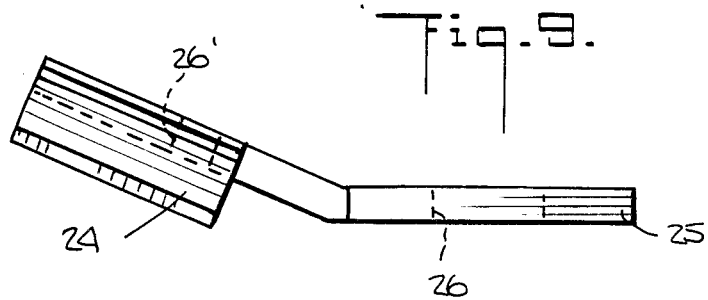
FIGS. 9, 10 and 11 are side, plan and end views, respectively, of the mandrel included in the embodiment of the invention shown in FIG. 2.

Structure:

Referring now to FIGS. 1, 2 and 3 in the drawings, a skin closure surgical stapling device in accordance with the invention comprises a housing formed of a complementary pair of injection-molded plastic parts 1 and 2. These housing parts are joined together by deformable plastic fasteners 3 which engage bosses 4, 5 and 6 (shown only in respect to housing part 2) and by welding along the mutually interengaging peripheral walls. Housing 1-2 is slotted along its underside 7 to receive a handle 8 formed of an injection-molded plastic material. Handle 8 is provided with integrally molded pivots which are received in respective short sleeves 10 molded integrally with housing parts 1 and 2.

A spring arm 11 which may be of leaf spring metal or plastic material, extends from an upper edge of handle 8 and abuts boss 6, the spring acting to urge the handle outwardly to the extended position illustrated in full line in FIG. 2. In this position, a nose portion of handle 8 abuts boss 5 to limit outward movement of the handle relative to the housing under the action of spring 11.

A former 12 defined by a sheet metal plate is so disposed in the housing as to be slidable relative thereto between an upper inoperative limit position and a lower operative limit position. Former 12 lies between boss 4 and the adjacent peripheral end walls of the respective housing parts 1 and 2 which define a guide for sliding movement of the former.

Boss 4 has a surface facing former 12 which is spaced from the adjacent wall of housing part 1, 2 by a distance which is only marginally greater than the thickness of the former. The width of former 12 is marginally less than the distance between the internal side faces of the housing so that the two housing parts 1 and 2 define a guide to ensure that former 12 does not become misaligned during its sliding movement.

At its lower or leading edge (as viewed in FIG. 6), former 12 is provided with a recess having an inner arched section 13 merging with a straight entry section 13E whose edges are chamfered. The arched section of recess 13 in the present embodiment is arcuate, but an angular three-sided geometric arch section is also envisaged, as illustrated by the geometric arch 13' shown in FIG. 7.

At its upper end, former 12 is provided with an offset lug 14 which is turned out of the general plane of former 12 so as to lie substantially perpendicular thereto. Lug 14 is received within a slot 15 formed in the nose of handle 8. The orientation and shape of slot 15 is such that, throughout movement of handle 8, it acts on lug 14 in a direction which is parallel to the intended direction of sliding movement of former 12.

A detent and release mechanism is provided for controlling sliding movement of former 12. This mechanism includes a pair of first parts 16 mounted on the upper edge of handle 8 (as viewed in FIG. 2) through the intermediary of a resilient support plate 17. Plate 17 and the first parts 16 are molded integrally with handle 8. The detent and release mechanism also includes a pair of second parts 18 which are molded integrally with the respective housing parts 1 and 2 so as to extend inwardly from the side walls thereof.

Each of first parts 16 includes a ribbed portion 16a whose ribs extend laterally relative to the direction of movement of the part during pivotal movement of the handle. Each first part 16 further includes a chamfered leading edge 16b and a portion 16c which is inclined with respect to the portion 16a and has a smooth surface. The portion 16c is inclined at an angle of about 45° to the general direction of movement of first part 16 and is disposed on the opposite side of first part 16 to the associated second part 18 when handle 8 is in the position shown in full line in FIG. 2; i.e., the inoperative position of former 12.

Each of second parts 18 includes a ribbed portion 18a whose ribs extend laterally relative to the direction of movement of first part 16. Each second part 18 further includes a chamfered leading edge 18b and a portion 18c which is inclined with respect to the portion 18a and which has a smooth surface. Portion 18c is inclined at an angle of about 45° to the general direction of movement of first part 16 and is disposed on the opposite side of second part 18 to the ribbed portion 18a. Portion 18c is disposed in the path of movement of portion 16c with the plate 17 in an unflexed condition (as illustrated in FIG. 2). As can be seen from FIG. 3, first parts 16 are supported only at their mutually inwardly-facing edge, whereas second parts 18 are supported only at their mutually outwardly-facing edges.

Provided in the lower region of the housing and adjacent to an outlet 19 therein is a staple indexer 20. The indexer, as best seen in FIG. 8, comprises a plastic rail 20a and a steel mandrel 20b. Plastic rail 20a extends into a magazine 21 (see FIG. 2) containing surgical closure elements in the form of a row of staples (not shown) which straddle the rail. The rail is joined to the housing by ultrasonic welding.

Figure 10:
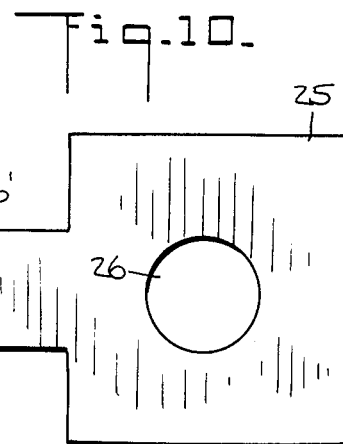
Figure 11:
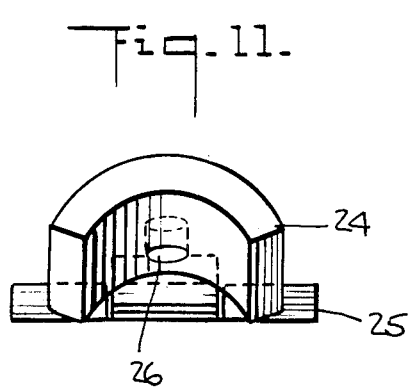

As shown in FIGS. 9 and 10, mandrel 20b has an arched position 24 and a plate-like anchor position 25, both portions having a locating hole (26 and 26'). The plastic rail 20a is formed by injection molding, one end of rail 20a being molded around anchor position 25 and part of the arched portion 24 of the mandrel so that the plastic material enters the locating holes 26 and 26' and serves to securely retain mandrel 20b in its position at the front end of the rail.

The arched portion 24 of the mandrel is of a shape and size corresponding to the arched recess 13 in former 12 (see FIG. 6). Mandrel 20b has a free end opposite anchor portion 25 which is embedded in the end 28 of rail 20a. The location for forming the staples lies between the free end of the mandrel and end 28 of rail 20a. End 29 of rail 20a is configured to form a pair of abutment surfaces 29 on either side of mandrel 20b where it joins rail 20a. These abutment surfaces 29 extend generally perpendicularly to the mandrel in a downward direction (i.e., on an opposite side of the mandrel to the former 12) and are adjacent the location for forming staples.

Operation:

In operation, former 12 acts upon the crosspiece of the staple on the mandrel and causes the side limbs thereof to abut against abutment surfaces 29 as it is being bent downwardly by former 12. The abutment of the staples against surfaces 29 during forming prevents the formation of a twisted staple.

The spring-biased pusher shoe 22 serves to urge the staples along rail 20a toward mandrel 20b at the forming location of the staples which is disposed in the path of movement of former 12. Abutment surfaces 29 are spaced from the housing parts 1 and 2 by a gap and lie at an angle of about 2° to the inner face of these parts, thus providing a tapered gap which is wider at the top than at the bottom between abutment surfaces 29 and housing parts 1 and 2. The minimum thickness of the gap is marginally less than the thickness of a staple.

Figure 12:
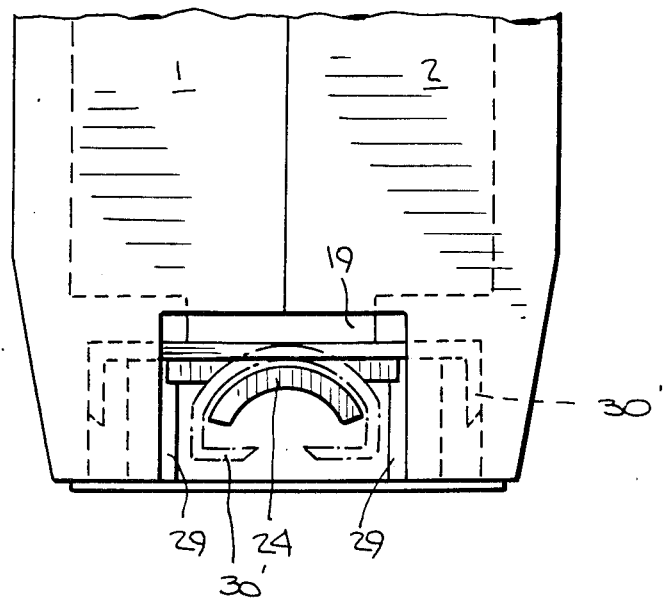
FIG. 12 is an end view of the embodiment of the invention shown in FIG. 1.

In operation, as shown in FIG. 12, a staple 30 will be retained on the mandrel if the handle is released when the staple is only partially formed because the depending limbs of the staple will be frictionally held between abutment surfaces 29 and the housing parts 1 and 2. When the staple is completely shaped to assume form 30', it is no longer held between the abutment surfaces and the housing and is of a shape capable of passing through outlet 19. This feature allows partial formation of the staple 30 prior to placing it over the skin incision and completing the closure without the danger of the partially formed staple dropping out of the device.

The surgical stapling device is positioned on the skin of the patient so that outlet 19 lies across the incision to be closed. Then by squeezing handle 8 against the action of the spring arm 11, this causes former 12 to be driven downwardly so that its lower end passes the mandrel 20b which is accommodated in the arched recess 13 at this stage. During squeezing of handle 8, the first parts 16 of the detent mechanism are moved toward the respective second parts 18 until leading edges 16b and 18b come into mutual engagement. Further movement of handle 8 causes leading edges 16b to ride over edges 18b, this being permitted by resilient flexing of support plate 17, so that the ribbed portions 16a and 18a come into mutual engagement.

The angles of inclination of the sides of the ribs on the ribbed portions 16a and 18a are chosen so that the ribs on the ribbed portions 16a can ride over the ribs of the ribbed portions 18c when handle 8 is squeezed. However, upon release of handle 8, movement of handle 8 and thus former 12 in the opposite direction under the action of spring arm 11 is prevented by interlocking the ribs of the ribbed portions 16a and 18a.

This interlocking action can occur at a plurality of positions intermediate the limit position of movement of former 12 because of a plurality of ribs are provided. Thus, close control over various stages in the formation of a staple can be exercised by the operator because the mechanism can hold handle 8 until the staple is finally closed. In this condition, first parts 16 have moved beyond the respective second parts 18 and, upon release of handle 8, spring 11 returns handle 8 and former 12 back to the original position (as shown in FIG. 2) because the plate 17 flexes back to its original position and brings the smooth portions 16c and 18c into alignment so that the parts 15 are free to ride back over the respective parts 18.

During the staple closing stage, the points of the staple enter the skin on opposite sides of the incision and the limbs bend inwardly toward each other so that the incision in the skin is closed thereby. It will be appreciated that deformation of the crosspiece of the staple occurs as a result of contact with mandrel 20b and with portions of the lower end of the former 12 on opposite sides of the arched recess 13.

The final arched shape of the crosspiece causes an arched air gap to exist between the skin incisions and the crosspiece of the staple even when the wound swells during healing. The portion of handle 8 under slot 15 abuts the upper surfaces of boss 14 to limit inward movement of the handle, thereby limiting movement of former 12 in the direction of mandrel 20b. This movement is arranged so that the free end of mandrel 20b is not so securely trapped between the staple and the skin that it cannot be removed when the staple has been fixed in position. The position of handle 8 at this stage is indicated in chain dot line in FIG. 2.

When handle 8 has been released, as described above, former 12 is clear of mandrel 20b so as to permit pusher shoe 22 to advance the row of staples to place a fresh staple in the path of movement of former 12. In order to give the operator an indication of the number of staples left in the magazine, a slot 23 is provided in housing part 2 adjacent magazine 27. Pusher shoe 22, which can be viewed through this slot 23, is preferably of a contrasting color to that of housing part 2. In this way, the position of shoe 22 can be readily seen, and the operator then knows the extent to which the staple supply has been depleted.

While there has been shown and described a preferred embodiment of SURGICAL STAPLING DEVICE in accordance with the invention, it will be appreciated that many changes and modifications may be made therein without, however, departing from the essential spirit thereof. Thus, a stapler may be made without the detent and release mechanism. And scale indicia may be inscribed along the edge of the housing under slot 23 so that the surgeon can use this scale to space the staples applied along the incision line.

I claim:

1. A surgical stapling device for forming and implanting a staple formed of a deformable wire and having a pair of parallel limbs bridged by a straight crosspiece into the skin of a patient undergoing a surgical procedure, the device comprising:
   A. a housing having an outlet;
   B. a rail disposed in the housing having a row of staples straddled thereon and a metal mandrel projecting from the front end of the rail into the outlet;
   C. pusher means on said rail to advance said row toward said mandrel to cause the foremost staple to be deposited on the mandrel, the mandrel being a solid plate and having an arched shape and being flanked on opposite sides by a pair of abutments on the front end of the rail;
   D. a plate-like former disposed in the housing, the leading edge of the former having a recess therein leading to a complementary arched section which conforms to the arched shape of the mandrel, said former being normally retracted from the mandrel to assume an inoperative position; and
   E. actuating means operatively coupled to the former to advance the former from its inoperative position to slide along the abutments at the front end of the rail to an operative position, in the course of which the mandrel is received within the recess in the former and the limbs of the staple engaged by the leading edge of the former are extended from the outlet to a degree sufficient to penetrate the skin of a patient on opposite sides of an incision to be closed, the deformable limbs being caused to bend inwardly by the coacting former and mandrel toward each other to close the incision, and the deformable crosspiece being bent to create an arched air gap above the skin to accommodate post-operative swelling.

2. A device as set forth in claim 1, wherein said rail is formed of plastic material and said mandrel is formed of steel.

3. A device as set forth in claim 1, wherein said pusher means is a spring-biased shoe which rides on said rail.

4. A device as set forth in claim 1, wherein the trailing end of the former is bent to form a lug for advancing the former.

5. A device as set forth in claim 4, wherein said actuating means is constituted by a handle which is pivoted to the housing and is biased to normally swing outwardly therefrom, said handle having a slot in its nose in which the former lug is received, whereby when the handle is swung inwardly toward the housing, the former is advanced thereby.

6. A device as set forth in claim 1, wherein said mandrel arch has an arcuate form, and said recess conforms thereto.

7. A device as set forth in claim 1, wherein said mandrel arch has a three-sided geometric form, and said recess conforms thereto.

8. A device as set forth in claim 1, wherein said housing is formed by a pair of complementary molded plastic pieces.

9. A device as set forth in claim 2, wherein said mandrel is provided with a blade-like rear anchor which is embedded in the front end of the plastic rail.

* * * * *